United States Patent [19]

Kelman

[11] Patent Number: 4,911,715
[45] Date of Patent: Mar. 27, 1990

[54] OVERLAPPING TWO PIECE INTRAOCULAR LENS

[76] Inventor: Charles D. Kelman, 721 Fifth Ave., New York, N.Y. 10022

[21] Appl. No.: 362,030

[22] Filed: Jun. 5, 1989

[51] Int. Cl.⁴ .............................................. A61F 2/16
[52] U.S. Cl. ...................................................... 623/6
[58] Field of Search ............................................. 623/6

[56] References Cited

U.S. PATENT DOCUMENTS

| 4,056,855 | 11/1977 | Kelman | 623/6 |
| 4,605,409 | 12/1986 | Kelman | 623/6 |
| 4,704,124 | 11/1987 | Shearing | 623/6 |
| 4,743,254 | 10/1988 | Davenport | 623/6 |

Primary Examiner—Ronald L. Frinks
Attorney, Agent, or Firm—Darby & Darby

[57] ABSTRACT

Overlapping two piece intraocular lens for successive insertion of the two pieces through a minimum size incision into the eye for assembly therein to form the two piece lens for implantation in the eye, including a lens body and a separate ring shaped collapsible filament, tension frame therefor containing light-masking material to inhibit light rays directed toward the lens body outer edge portions from being scattered thereby toward the retina after the assembled overlapping two piece lens has been implanted in the eye.

16 Claims, 2 Drawing Sheets

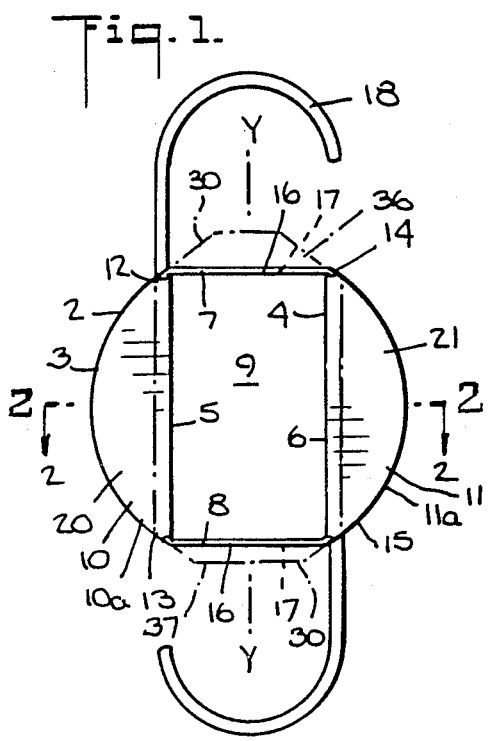

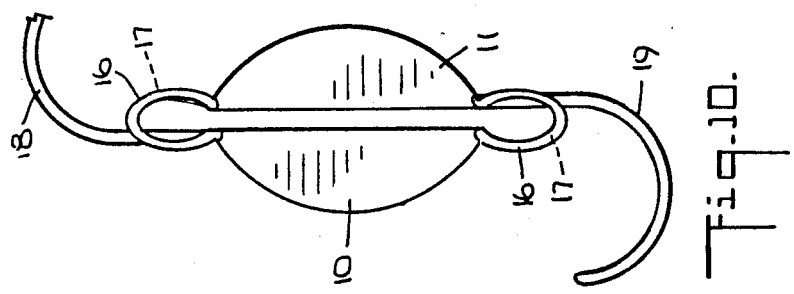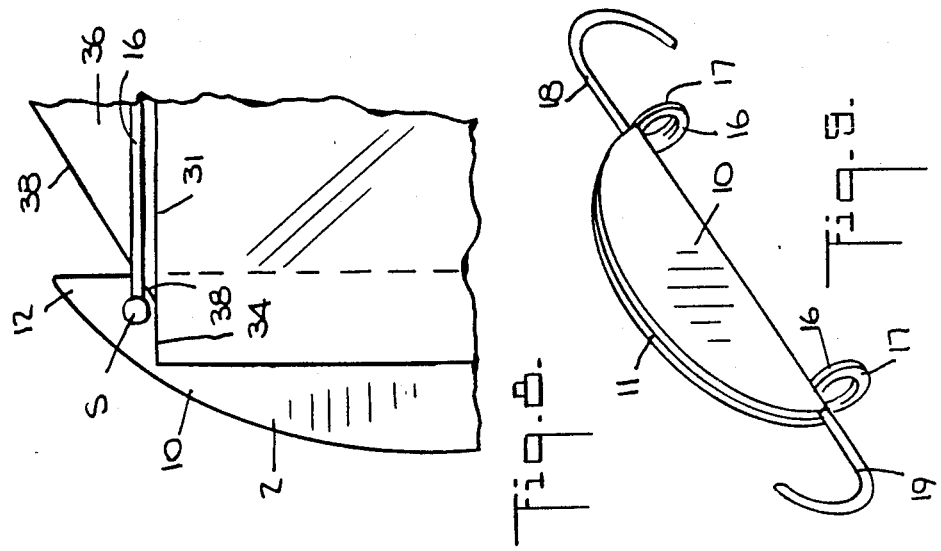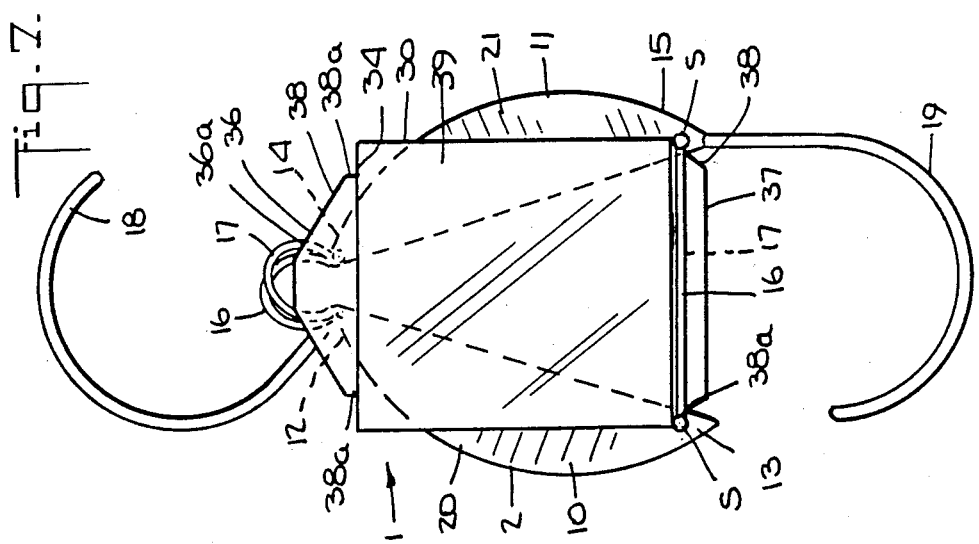

OVERLAPPING TWO PIECE INTRAOCULAR LENS

FIELD AND BACKGROUND OF THE INVENTION

The present invention relates to an overlapping two piece intraocular lens, and more particularly to an artificial intraocular lens for implantation in an eye, e.g in the posterior chamber, after extracapsular removal of the natural lens, wherein the two pieces are independently successively inserted through a minimum size incision into the eye for assembly therein to form the two piece lens, and include a lens body or optic and a separate ring shaped collapsible filament, tension frame therefor containing light masking means for inhibiting light rays directed toward the lens body outer edge portions from being scattered thereby toward the retina after the assembled overlapping two piece lens is implanted in the eye.

For treating conditions such as natural eye lens cataracts, a known eye surgery procedure is to remove the cataracted lens through a minimum size incision in the wall of the cornea of the eyeball, and replace it by an artificial intraocular lens as an internal implant. One surgical procedure involves the extracapsular removal of the natural lens, leaving portions of the posterior lens capsule intact as a positioning site for implanting the intraocular lens in the eye.

U.S. Pat. No. 4,605,409 to Kelman discloses a one piece intraocular lens of the above type, having a small size lens body or optic, flexible position fixation haptics, and deformable masking means, such as laterally disposed flat planar wings temporarily contracted to provide the lens with a reduced girth permitting insertion through such a minimum size corneal incision into an eye. Upon implantation, the wings mask the optic side edge portions to overcome the edge glare effect of otherwise scattered incoming light rays at the peripheral marginal regions of the small size lens, such light masking being achieved by leaving the wing surfaces in rough, unground, condition, or by providing an opaque coating thereon.

U.S. Pat. No. 4,056,855 to Kelman shows a two piece intraocular lens, including an elliptically shaped lens member formed of a central lens body or optic and end tongues, and a separate similarly shaped non-collapsible, continuous closed loop wire frame resiliently self-clampable only to the lens body, once the two pieces are independently inserted through a minimum size corneal incision into an eye for like implantation purposes. The frame ends are arranged in the posterior chamber behind the iris and the lens member end tongues are arranged in the anterior chamber in front of the iris, both serving as position fixation means, while the optic is situated across the pupil. No light masking means of the above type are present.

U.S. Pat. No. 4,596,578 to Kelman shows a two piece intraocular lens, including a generally rectangularly shaped lens body or optic and a separate frame having a similarly shaped noncollapsible split ring formed of cantilever flexible arms for embracingly receiving the optic and also serving as light masking means, and cantilever end limbs as position fixation means, the two pieces being independently inserted through a minimum size incision into the eye for assembly therein. The split ring is needed to permit the flexible arms to be separated for snaking the resulting open ring conformation through the incision and thereafter for enclosing the flexible arms around the optic to assemble the lens prior to implantation.

U.S. Pat. No. 4,704,124 to Shearing shows a multipart intraocular lens whose parts are preassembled as a foldable, interconnected unit prior to insertion into the eye, whereupon the unit is folded onto itself to reduce its girth for insertion, and then unfolded for implanting the lens in the eye. The multiple side by side lens parts are indirectly interconnected by seating their outer margins in a groove of a foldable ring frame part which embraces the lens parts, or by hinge, membrane or outwardly extending strand loop connections directly between adjacent lens parts in frameless units, all without tension connection or overlapping arrangement of the lens parts, or use of the above noted light masking means.

It would be desirable to provide a minimum size intraocular lens for implantation in an eye, following extracapsular removal of the natural eye lens, permitting rapid and efficient lens insertion through the same minimum size corneal incision used to remove the natural lens, and at the same time provide light masking means for the lens body, while utilizing a structurally simple and stable arrangement of parts, readily made at relatively low cost from widely available materials.

SUMMARY OF THE INVENTION

It is an object of this invention to overcome prior art drawbacks, and to provide an overlapping two piece artificial intraocular lens for successive insertion of the two separate pieces through a minimum size incision into an eye for assembly in situ therein to form the two piece lens for implantation, e.g. after extracapsular removal of the natural eye lens, the two piece lens including a minimum width lens body or optic and a separate ring shaped collapsible filament, tension frame for the optic, having light masking means for inhibiting light rays directed toward the outer edge of the optic from being scattered thereby toward the retina after lens implantation.

It is an another object of this invention to provide a lens of the stated type, of minimum insertion width individual pieces permitting maximum accommodation of a small size optic through a minimum size eye incision, plus a frame therefor that does not require a larger incision than needed for the optic, and which can be rapidly and efficiently inserted into the eye, assembled therein as a stable, stiff, tensioned unit and then implanted, and still provide light masking for the optic.

It is a further object of this invention to provide such a lens, which can be made at relatively low cost from widely available material of desired characteristics, using a structurally simple and stable arrangement of cooperating parts.

According to this invention, an overlapping two piece artificial intraocular lens is provided for successive independent insertion of the two pieces through a minimum size incision into the eye for assembly therein to form the two piece lens for implantations in the eye, e.g. following extracapsular removal of the natural eye lens.

The two piece intraocular lens comprises a generally planar lens body having two opposed length sides and two opposed width sides, each width side having a stabilizer formation disposed laterally therealong and extending peripherally outwardly therefrom, and a separate, generally planar, continuous and uninterrupted ring shaped collapsible filament, tension frame, having an outer, e.g. circular, boundary edge and an inner edge defining an aperture with two opposed length sides and two opposed width sides and sized and shaped for overlapping registry with the lens body.

The frame includes two opposed length side oblong planar wing members defining light masking means and two opposed width side collapsibly deformable, locally flexible but essentially unstretchable, linear tension filament means laterally interconnecting correspondingly adjacent ends of the wing members at opposed connection sites thereon to form the frame and define the aperture therewithin.

Each opposed filament means is sized and arranged to receive and grippingly embrace between the opposed connection sites thereat a corresponding stabilizer formation for mounting the lens body under positive tension thereby on the frame with the lens body length sides in overlapping relation to the adjacent portions of the wing members along the aperture length sides for assembling the two pieces as a self connected, generally stiff planar unit.

The two opposed filament means each comprises preferably a pair of closely side by side locally flexible but essentially unstretchable linear tension filaments laterally interconnecting correspondingly adjacent ends of the wing members at the opposed connection sites thereon, with each opposed pair of filaments being sized and arranged to receive and grippingly embrace therebetween and between the opposed connection sites thereat a corresponding stabilizer formation.

Significantly, the connection sites are located on the surfaces of the wing members which face the lens body when the two pieces are assembled, each formation has a selective length in the width direction, and each pair of filaments has opposed filament ends connected to the opposed wing member end thereat at correspondingly opposed connection sites on the wing member surfaces which face the lens body so as to define a slit bounded by the filaments and having a length in the width direction between the connection sites which corresponds sufficiently to that formation length for receiving the formation in the slit under gripping tension between the connection sites to prevent relative displacement of the two pieces in the width direction.

Each formation, which is favorably formed as a generally planar tab, may have opposed side edges facing generally in the same direction as the lens body length sides and which are engaged grippingly by the portions of the corresponding pair of filaments at the opposed connection sites when the formation is received in the slit. For efficient assembling of the unit, at least one formation is formed as a planar tab of generally triangular shape and peripherally outwardly converges to an intermediate apex portion to facilitate receiving the tab in the slit.

The lens body may have an outer edge forming a seating shoulder with each formation to engage at least one of the corresponding pair of filaments under gripping tension to prevent relative displacement of the two pieces in the length direction.

Desirably, the lens body and wing members are made of shape retaining plastic, and each filament is made of plastic which is essentially unstretchable in the direction of the filament axis but locally deformable in a direction crosswise of that axis to permit filament flexing relative to that axis.

Each wing member may have an anterior surface of conforming shape to the lens body posterior surface and arranged for corresponding overlapping contact in offset planar, stabilizing surface to surface relation therewith when the two pieces are assembled.

Position fixation means are desirably provided for seating the lens in the eye, such as a haptic connected to each wing member. Also, the wing member light masking means may comprise optically opaque means or optically translucent means.

In a preferred form, the lens body has a generally rectangular oblong shape, the frame has a generally circular outer edge, and the wing members each have the shape of a segment of circle whose chord is defined by a corresponding length side of the inner edge forming the aperture.

BRIEF DESCRIPTION OF THE DRAWINGS

Other objects of the invention will become apparent from the within specification and accompanying drawings, in which:

FIG. 1 is a plan view of the anterior side of a planar, continuous and uninterrupted ring shaped collapsible filament, tension frame, having light masking wing members and haptics, and forming one piece of the overlapping two piece intraocular lens according to an embodiment of the invention;

FIG. 2 is a sectional view taken along line 2—2 of FIG. 1;

FIGS. 3, 4 and 5 are anterior side plan, top end, and left lateral side, views, respectively, of the lens body or optic forming the other separate piece of the two piece intraocular lens used with the frame of FIG. 1;

FIG. 6 is an exaggerated schematic top end view of the two piece lens in assembled state as it would exist in the eye;

FIG. 7 is an exaggerated front elevational view showing the manner in which the two pieces may be assembled in the eye;

FIG. 8 is an enlarged view similar to FIG. 7 showing a portion of the coating mounting structure;

FIG. 9 is a perspective view of the frame of FIG. 1 folded onto intself to form a minimum size collapsed condition insertable compact unit; and FIG. 10 is a plan view showing the wing members of the frame of FIG. 1 drawn into abutment with each other to form another minimum size collapsed condition insertable compact unit analogous to that shown in FIG. 9.

DESCRIPTION OF THE PREFERRED EMBODIMENTS

Referring to the drawings, and initially to FIGS. 1-2, a generally planar, continuous and uninterrupted ring shaped collapsible filament, tension frame 2 is shown, constituting one piece of an overlapping two piece artificial intraocular lens 1 (FIG. 7), according to one embodiment of the invention, in which the other piece is a generally planar, oblong lens body or optic 30 of generally rectangular shape (FIGS. 3-5).

Frame 2 has a generally circular outer boundary edge 3, and an inner edge 4 defining an oblong central aperture 9, to overlap rectangular like optic 30, with two opposed length sides or longer sides 5,6 and two opposed width sides or shorter sides 7,8, sized and shaped to register overlappingly with optic 30 (shown in phantom in FIG. 1).

Frame 2 includes two opposed longer side oblong planar wing members or wings 10,11, which define light masking means 10a,11a, such as by providing wings 10,11 as opaque or translucent members, or with opaque or translucent surfaces. Wings 10,11 have generally pointed tips or ends 12,13 and 14,15, respectively. Frame 2 also includes two opposed shorter side collapsibly deformable filament means, such as two pairs of closely side by side, or parallel, locally flexible but essentially unstretchable linear tension filaments or strands 16,17, which laterally interconnect correspondingly adjacent wing ends 12,14, and 13,15, at opposed connection sites S,S thereon to form frame 2 and its aperture 9.

When frame 2 is in normal uncollapsed planar disposition, the respective anterior, e.g. flat, surfaces 20,21 and posterior, e.g. flat, surfaces 22,23 of wings 10,11, are in corresponding, e.g. coplanar or flat, alignment (FIG. 2).

As shown in FIGS. 3-5, optic 30 has an outer boundary edge 31 with two opposed length sides or longer sides 32,33 and two opposed width sides or shorter sides 34,35, each shorter side having a stabilizer formation 36 or 37, e.g. a generally planar, stiff or rigid tab, respectively disposed laterally therealong and extending peripherally outwardly therefrom, i.e. in the plane of optic 30. Tabs 36,37 each have a set of opposed, e.g. outwardly converging taper, side edges 38,38 facing in the same direction as optic longer sides 32,33.

Each of tabs 36,37 is desirably provided with a generally triangular shape such that it peripherally outwardly converges to an intermediate apex portion 36a or 37a to aid mounting of optic 30 on frame 2 as later described, although optionally one such tab, i.e. the first to be mounted, e.g. tab 37, may have a stunted or truncated taper shape, such as a trapezoidal shape.

Tabs 36,37 may optionally define additional light masking means by providing them as opaque or translucent members, or with opaque or translucent surfaces, in analogous manner to light masking means 10a,11a of wings 10,11.

Optic 30 also has an anterior, e.g. curved, surface 39 and a posterior, e.g. flat, surface 40, forming a selective profile to achieve the desired optical refractive characteristics for the lens, in a known manner.

Each opposed pair of filaments 16, 17 is sized and arranged to receive and grippingly embrace therebetween and between the opposed connection sites S,S thereat a corresponding tab 36 or 37 for mounting optic 30 under positive tension thereby on frame 2, with optic longer sides 32,33 in overlapping relation to the adjacent portions of wings 10,11 along aperture longer sides 5,6 for assembling the two pieces as a self connected, generally stiff planar unit (FIG. 6).

Specifically, the connection sites S,S are favorably located on wing anterior surfaces 20,21 which face optic posterior surface 40 when the two pieces are assembled (cf. FIG. 2), tabs 36,37 each have a selective length L in the width direction between the lateral ends of edges 38,38, i.e. along lateral or horizontal axis X (FIGS. 1 and 6), and each pair of filaments 16,17 has opposed ends connected to the opposed wing ends 12,14 and 13,15 thereat at correspondingly opposed sites S,S on wing anterior surfaces 20, 21, as the case may be.

This construction is arranged at such facing wing anterior surfaces 20,21 so as to define a slit bounded by the given pair of filaments 16,17 and having a length in the width direction between the given set of opposed sites S,S which corresponds sufficiently to, e.g. essentially equals, tab length L for receiving tab 36 or 37 in such slit under gripping tension between the set of sites S,S, to prevent relative displacement of the two pieces in the width direction.

Thus, each set of tab edges 38 is engaged grippingly by the portions of the corresponding pair of filaments 16,17 at the opposed sites S,S when tab 36 or 37 is received in the corresponding slit (FIG. 6). For precise arrangement of optic 30 relative to frame 2 in lens 1, tabs 36,37 are preferably flat and located flush with optic posterior surface 40 and thus as close as possible, i.e. in the transverse direction of optical axis Z of optic 30 (FIG. 5), to the level of the corresponding pair of filaments 16,17, i.e. extending in the direction of lateral axis X, for efficient tension gripping of tabs 36,37 by the corresponding pairs of filaments 16,17 in balanced manner with all forces uniformly distributed at all points of the opposed interconnections of the two pieces.

To enhance this close planar relationship, each set of sites S,S for connecting the filament ends of the given pair of filaments 16,17 to wings 10,11 is likewise preferably located flush with wing anterior surfaces 20,21, such that the filaments 16,17 thereat extend in substantially coplanar relation to tab 36 or 37, as the case may be (FIG. 6).

Optic outer edge 31 favorably forms a seating shoulder with each of tabs 36 and 37, i.e. in general lateral alignment along optic shorter sides 34 and 35 with the given opposed set of sites S,S thereat, for engaging at least one of the corresponding pair of filaments 16,17 under gripping tension to prevent relative displacement of the two pieces in the length direction, i.e. along longitudinal or vertical axis Y (FIG. 1). Thus, where tabs 36,37 are flush with optic posterior surface 40, one of filaments 16,17 at each tab will engage the tab posterior face while the other filament will engage the seating shoulder formed by both the tab anterior surface and the adjacent portion of optic outer edge 31 (FIGS. 5 and 6).

Preferably, wing anterior surfaces 20,21 are of conforming shape to optic posterior surface 40, e.g. of like flat profile, and suitably arranged for overlapping contact in offset planar, stabilizing surface to surface relation with posterior surface 40 when frame 2 and optic 30 are assembled as lens 1 (FIG. 6).

Necessarily, the dimensions of aperture 9 and optic 30, and the length of filaments 16,17 and tabs 36,37, will be selected and matched with each other to assure that optic 30 will be lodged in the slits formed by the opposed pairs of filaments 16,17 to align it centrally in aperture 9 and hold it in frame 2 under slight tension, as described below. At the same time, filaments 16,17 will necessarily be self-collapsibly deformable to assure temporary collapse of frame 2 for insertion through the minimum size corneal incision.

While frame 2 may be seated via wings 10,11 as position fixation means in the eye, e.g. in the posterior chamber remaining after extracapsular removal of the natural lens, preferably lens 1 includes opposed haptics 18,19 as, e.g. limitedly flexible, position fixation means, in the usual manner, such as on frame 2 with haptic 18 connected to end 12 of wing 10 and haptic 19 connected to the diagonally opposite end 15 of wing 11 and lying in the plane of frame 2.

The connections between wings 10,11 and filaments 16,17 at sites S,S and those between haptics 18,19 and wing ends 12,15, are preferably integral connections. In particular, filaments 16,17 may be formed as a pair of strands coming together at their opposite ends to form a single or common end strand or filament, which may be for instance either integrally molded with wings 10,11 at their corresponding wing ends 12,14 and 13,15, or integrally held in corresponding openings in such wing ends 12,14 and 13,15, i.e. at wing anterior surfaces 20,21 (FIG. 2), in the manner in which associated haptics are conventionally assembled to or mounted on intraocular lenses.

As shown in FIG. 6, the coplanar alignment of and overlapping relation, and especially overlapping contact, between the parts provides a stiff and stable tension connection between frame 2 and optic 30, i.e. especially with tabs 36,37 in close planar alignment with the planar level of the corresponding pairs of filaments 16,17 for more precise coplanar tension connection of the overlapping portions of wings 10,12 and optic 30. In this way, the bilateral disposition of each pair of filaments 16,17 surrounding and grippingly embracing a given tab 36 or 37 prevents relative displacement of the two pieces, not only laterally along axis X and longitudinally along axis Y but also rotationally about their overlapping longer sides.

Since the end portions of each pair of filaments 16,17 at sites S,S on wings 10,11 grippingly embrace the opposed side edges 38 of each tab under positive tension, lateral displacement is per se prevented, and for the same reason longitudinal displacement is prevented, because at least one filament of each pair will also be in retaining tension contact with the adjacent portion of optic outer edge 31, as where the latter forms a shoulder with the tab thereat.

On the other hand, due to the lateral tension embracing of the intermediate spans of filaments 16,17 of each pair against the opposing anterior and posterior faces of the corresponding tab 36 or 37, rotational movement of either wing 10 or 11 relative to optic 30 about an axis parallel to longitudinal axis Y and located at either overlapping set of wing and optic longer sides 5 and 32, or 6 and 33, as the case may be, will be prevented, especially where optic posterior surface 40 is in overlapping coextensive surface to surface stabilizing contact with wing anterior surfaces 20 and 21 (FIG. 6).

It will be noted that each pair of filaments 16,17, acting as a double strand connection, inherently distributes all tension forces uniformly and in every crosswise direction relative to the given filament axis. This would not be so if a strap of even minimal width, having a central slot longitudinally therealong, were used instead to grip a given tab, as the strap would constitute a two dimensional plate only flexible in a perpendicular direction out of its own plane but not flexible within its own plane, and thus a local portion thereof could not be deformed in a direction crosswise of its longitudinal axis but within that plane for proper distribution of forces.

In contrast thereto, each filament of the invention, inherently being of substantially round or uniform cross section, is capable of being flexed in every direction relative to its axis while only being incapable of stretching in the direction of that axis, thereby enabling all forces to be uniformly distributed and freely applied in unhindered manner for balanced stable connection for the two pieces as assembled.

Indeed, the use of a pair of filaments 16,17 at each shorter side of frame 2 provides a balanced, robust tension connection eliminating all risk of optic 30 slipping out from its position in frame 2 after implantation of lens 1 in the eye, and affords essentially complete safety as to maintaining securely optic 30 in attached relation to wings 10,11.

In accordance with one well known surgical procedure, for example, the surgeon will remove the natural lens and a portion of the anterior wall part of the natural lens capsule via the usual small size corneal incision, e.g. 3 mm, leaving intact the posterior wall part of the lens capsule, which is held in place by the zonules or suspensory ligament and fibers attached to its external periphery. The internal periphery of the posterior wall part forms a recessed anterior cul-de-sac or ciliary sulcus which efficiently serves as a posterior chamber seating location for the haptics of the intraocular lens.

As above noted, optic 30 and aperture 9 of frame 2 are of complemental matching overlapping size and shape, while the length L of tabs 36,37 and that of each pair of filaments 16,17 between opposed connection sites S,S are essentially equal.

Thus, as schematically shown in FIG. 7, after successive insertion of two pieces through the corneal incision into the eye, stiff triangular tab 37, i.e. guided via its facilitating tapered edges 38, may be placed in the slit formed between one pair of filaments 16,17, with optic posterior surface 40 resting at optic longer sides 32,33 against wing anterior surfaces 20,21 at the adjacent portions of wings 10,11 along wing longer sides 5,6 to align the main portion of optic 30 inwardly of its peripheral margins with aperture 9, e.g. such that tab 37 is seated in the slit formed between the pair of filaments 16,17 thereat and pushed into tension position.

Then, wings 10,11 may be tilted slightly toward each other by the surgeon at wing ends 12,14, by rotation about sites S,S on wing ends 13,15 at the side edges 38 of the already seated tab 37 as pivot points, so as to provide slack in the intermediate span of filaments 16,17 at wing ends 12,14. This tilting enables the surgeon to lift one slackened filament, e.g. filament 16, upwardly or peripherally outwardly and transversely across or over apex portion 36a of stiff triangular tab 36 as a "looped" filament which fits over tab 36, while keeping the other slackened filament, e.g. filament 17, as an "unlooped" filament on the remote planar side of tab 36.

Thereafter, wings 10,11 may be tilted away from each other back to their normal erect positions while the "looped" filament rides along the tapered side edges 38 of tab 36, with both filaments becoming increasingly tightened until they reach their final locked condition, being lodged into tension position to complete the mounting when longer sides 5 and 6 become generally parallel to one another, whereby to form the assembled two piece intraocular lens 1 in situ in the eye.

Providing tabs 36,37 with outwardly converging tapered side edges 38 facilitates insertion of each tab in its slit, the taper being pronounced at least for tab 36, as the final tab to be mounted, so as to define a triangular shape with a reduced span apex portion 36a aiding the looping over of one slackened filament onto the other lateral side of tab 36 to lock the filaments, as optic 30 is lodged into position via its tabs in tension connection with the opposed pairs of filaments.

As shown in FIG. 8, the incline of each tab edge 38 at its end portion closest to the given site S thereat, permits composite self-adjusting width and length positioning of optic 30 in frame 2 and its centering relative to aperture 9, by direct abutting contact at an appropriate point on that edge 38 incline with the ends of filaments 16,17 at that given site S when optic 30 is lodged in final tension position.

As the procedure for assembling lens 1 involves the stated tilting of wings 10,11, optic 30 and wings 10,11 must be arranged in overlapping relation to allow for the rotational sliding of wings 10,11 underneath, i.e. posteriorly of, optic 30 in the close confines of the eye (FIG. 7). Hence, no part of optic 30 can extend into the aperture 9 space between wings 10,11 as this would impede the sliding wing movement needed to provide slack in the "looped" filament at triangular tab 36, once tab 37 is in place, to loop that filament over apex portion 36a to lodge tab 36 between its filaments 16,17.

By locating the connection sites S,S for each pair of filaments 16,17 suitably on wing anterior surfaces 20,21 which are adjacent and slide against optic posterior surface 40, i.e. by locating sites S,S on the surfaces of wings 10,11 which face and slide against the adjacent surface of optic 30, yet at the outer tips or wing ends 12,14 and 13,15 and thus suitably beyond the range of the regions of the surface of optic 30 against which wings 10,11 slide during their tilting movement, each pair of filaments 16,17 efficiently embraces its tab 36 or 37 as close to the sliding interface between optic 30 and wings 10,11 as possible for maximum stability of the assembly.

Preferably, one of haptics 18,19 will first be positioned in the usual way in its desired location, e.g. in the posterior chamber, to stabilize frame 2, then optic 30 will be placed in juxtaposition with frame 2 and lodged into place as above described, and thereafter the other of haptics 18,19 will be positioned in its desired location, e.g. also in the posterior chamber, whereby to complete the lens implantation.

The two piece construction of lens 1 facilitates exploitation of the minimum size corneal incision used by the surgeon for extracapsular removal of the natural eye lens, since each of the two pieces 2 and 30 may be separately successively independently inserted through that same minimum size incision into the eye for assembly therein. This is particualarly significant since, understandably, the smaller the corneal incision size the less the trauma experienced by the patient, and in turn the less the pain and discomfort endured then and thereafter, not only because of the incision itself but also because of the number and/or sizw of any needed sutures.

Thus, because filaments 16,17 are made of self-collapsible, locally flexibly deformable material, wings 10,11 may be simply folded onto each other as shown in FIG. 9, or drawn in side by side abutting relation, e.g. in the same plane, as shown in FIG. 10, or the like, each such appropriate form representing a minimum girth compact unit readily longitudinally insertable through that same minimum size incision. By preferably providing optic 30 with an oblong shape, its width may be conformed to the size of that same incision whereby to provide a likewise minimum girth compact unit, as shown in FIG. 4, readily longitudinally insertable through such incision, after which the two pieces may be assembled into lens 1 as shown in FIG. 6, and schematically in FIG. 1.

The self-collapsibly deformable nature of frame 2 is due to the locally flexible characteristic of the material of which filaments 16,17 is made, whereas the positive tension gripping of tab 36,37 to provide lens 1 as a self connected, generally stiff planar unit of maximum stability is due to the essentially unstretchable characteristic of such filament material.

Thus, the filaments must be locally deformable in a direction crosswise of the filament axis to permit facile flexing of the filament relative to that axis to achieve the stated insertion of frame 2 in collapsed form into the eye. At the same time, the filaments must be essentially unstretchable in the direction of the filament axis to achieve the stated tension connection of the two pieces as assembled in the eye.

Both of the above characteristics are achieved by making filaments 16,17 of minimum cross sectional thickness plastic material, and using polymethylmethacrylate (PMMA) or similar material as the plastic, while precisely determining the length of filaments 16,17 and tabs 36,37 to assure the holding of optic 30 in frame 2 under slight but positive tension.

On the other hand, wings 10,11, as well as haptics 18,19, are conveniently provided of suitable shape retaining, yet optionally limitedly resilient or flexible, plastic material such as polymethylmethacrylate (PMMA), although they may also be made of polypropylene or silicone plastic should enhanced deformable characteristics for these parts be especially desired. Optic 30 is preferably made of rigid polymethylmethacrylate (PMMA) so that is may be readily lodged into position via its stiff or rigid tabs 36,37, as aforesaid.

Of course, the optic will be formed of suitable light focusing material having the desired optical characteristics, and all materials used for the two piece lens must be compatible with the eye fluid environment in the eyeball interior, and thus must be non-toxic. After the two pieces are inserted, assembled and implanted by the surgeon, they will advantageously retain their desired optical and other characteristics.

Favorably, optic 30 has a maximum dimension in the width direction of about 3 mm, and wings 10,11 each have a maximum dimension in the width direction of about 1.6 mm. These dimensions are readily accommodated in a minimum size corneal incision of for instance about 3 mm.

Referring to FIGS. 1 and 3, circular outer edge 3 of frame 2 preferably has a diameter of about 6 mm, which is generally considered the proper average size for an intraocular lens, and wings 10,11 have a maximum width at their widest crest portions of about 1.6 mm, so as to provide aperture 9 with a shorter side width of about 2.8 mm, i.e. along horizontal axis X, and a longer side length of about 5.5 mm, i.e. along vertical axis Y, with the pairs of filaments 16,17 representing truncated ends located at a maximum distance of about 0.25 mm each from the extension of the circle projection of outer edge 3 thereat.

Optic 30 will have similar dimensions to aperture 9, i.e. a shorter side width of about 3 mm and a longer side length of about 5.5 mm, thereby assuring the tension held disposition of optic 30 in frame 2 with optic 30 overlapping wings 10,11 to provide a 2.8 mm width opening as masked by aperture 9. The thickness of optic 30, i.e. along transverse optical axis Z (FIGS. 4–5), will depend on the selected optical characteristics of optic 30. However, as may be seen from FIGS. 2 and 4 to 6, wings 10,11 are generally of thin, flat cross section compared to the thickened conventional size rounded anterior curvature cross section of optic 30, e.g. with such optic having a maximum thickness dimension of about 1.5 mm.

In terms of the geometrical shape of the generally oblong rectangular embodiment per frame 2, it will be seen that wings 10,11 form opposed longitudinal edges of frame 2, or more precisely of central aperture 9, which constitute segments of the circle bounded by circular outer edge 3, such that the elongated edges represented by longer sides 5,6 define chords of that circle. Also, the arrangement of the various parts of frame 2 and optic 30 is such that a diametrically symmetrical configuration is desirably provided, including preferably the diametrically opposed symmetrical disposition of haptics 18,19 on frame 2 with their curves extending in opposite directions.

It is clear from the foregoing that the two piece lens assembly of the invention constitutes a structurally simple arrangement of cooperating parts forming a unit which is readily fabricated at relatively low cost from widely available materials of desired characteristics.

The coaction of the tabs and their pairs of filaments in assembling the lens serves (a) to maintain the frame in expanded, generally flat, condition, and (b) to fix the optic generally centrally relative to the frame and its aperture. Also, the overlapping edge relation between the inner longer sides of the light masking wings and the outer longer sides of the optic serves to shield the retina from light rays impinging on the optic edges thereat. Thus, the invention construction is more easily manufactured, and more easily assembled in the eye, and once assembled constitutes a self supporting, stiff and stable unit readily implanted in the eye.

It will be understood that the surgical procedures contemplated herein are well known to those skilled in the art, and that the nature and significance of the masking means as they relate to the small size optics herein are the same as described in the aforesaid U.S. Pats. Nos. 4,605,409 and 4,596,578.

By reason of the simple two piece construction involved, should it be found desirable or necessary at some future time, a new corneal incision can be made, the optic conveniently dislodged from the frame and removed from the eye through the new incision while the frame remains in place, and a new optic, perhaps of different refractive characteristics, inserted in the original frame as is, or after temporarily extracting one haptic from its posterior chamber position to facilitate reassembly before repositioning the haptic.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Overlapping two piece intraocular lens for successive insertion of the two pieces through a minimum size incision into the eye for assembly therein to form the two piece lens for implantation in the eye, which comprises
    a generally planar lens body having two opposed length sides and two opposed width sides, each width side having a stabilizer formation disposed laterally therealong and extending peripherally outwardly therefrom, and
    a separate, generally planar, continuous and uninterrupted ring shape collapsible filament, tension frame having an outer boundary edge and an inner edge defining an aperture with two opposed length sides and two opposed width sides and sized and shaped for overlapping registry with the lens body,
    the frame including two opposed length side planar wing members defining light masking means and two opposed width side collapsibly deformable, locally flexible but essentially unstretchable, linear tension filament means laterally interconnecting correspondingly adjacent ends of the wing members at opposed connection sites thereon to form the frame and define the aperture therewithin,
    each opposed filament means being sized and arranged to receive and grippingly embrace between the opposed connection sites thereat a corresponding stabilizer formation for mounting the lens body under positive tension thereby on the frame with the lens body length sides in overlapping relation to the adjacent portions of the wing members along the aperture length sides for assembling the two pieces as a self connected, generally stiff planar unit.

2. Lens of claim 1 wherein the two opposed filament means each comprises a pair of closely side by side locally flexible but essentially unstretchable linear tension filaments laterally interconnecting correspondingly adjacent ends of the wing members at the opposed connection sites thereon, each opposed pair of filaments being sized and arranged to receive and grippingly embrace therebetween and between the opposed connection sites thereat a corresponding stabilizer formation.

3. Lens of claim 2 wherein the connecting sites are located on the surfaces of the wing members which face the lens body when the two pieces are assembled, each formation has a selective length in the width direction, and each pair of filaments has opposed filament ends connected to the opposed wing member ends thereat at correspondingly opposed connection sites on the wing member surfaces which face the lens body so as to define a slit bounded by the filaments and having a length in the width direction between the opposed connection sites which corresponds sufficiently to the formation length for receiving the formation in the slit under gripping tension between the connection sites to prevent relative displacement of the two pieces in the width direction.

4. Lens of claim 3 wherein each formation has opposed side edges facing generally in the same direction as the lens body length sides and which are engaged grippingly by the portions of the corresponding pair of filaments at the opposed connection sites when the formation is received in the slit.

5. Lens of claim 4 wherein each formation is in the form of a generally planar tab.

6. Lens of claim 5 wherein at least one of the tabs is of generally triangular shape and peripherally outwardly converges to an intermediate apex portion to facilitate the receiving of the tab in the slit.

7. Lens of claim 2 wherein the lens body has an outer edge which forms a seating shoulder with each formation for engaging at least one of the corresponding pair of filaments under gripping tension to prevent relative displacement of the two pieces in the length direction.

8. Lens of claim 2 wherein the lens body and wing members are made of shape retaining plastic, and each filament is made of plastic which is essentially unstretchable in the direction of the filament axis but locally deformable in a direction crosswise of the filament axis to permit flexing of the flexing relative to its axis.

9. Lens of claim 1 wherein the lens body has a posterior surface and each wing member has an anterior surface of conforming shape to the lens body posterior surface and arranged for corresponding overlapping contact in offset planar, stabilizing surface to surface relation therewith when the two pieces are assembled.

10. Lens of claim 1 wherein the lens body has a maximum dimension in the width direction of about 3 mm, and the wing members each have a maximum dimension in the width direction of about 1.6 mm.

11. Lens of claim 1 wherein position fixation means are provided for seating the lens in the eye.

12. Lens of claim 11 wherein the position fixation means include a haptic connected to each wing member.

13. Lens of claim 1 wherein the light-masking means comprise optically opaque means.

14. Lens of claim 1 wherein the light-masking means comprise optically translucent means.

15. Lens of claim 1 wherein the lens body has a generally rectangular shape, the frame has a generally circular outer edge, and the wing members each have the shape of a segment of a circle whose chord is defined by a corresponding length side of the inner edge forming the aperture.

16. Overlapping two piece intraocular lens for successive insertion of the two pieces through a minimum size incision into the eye for assembly therein to form the two piece lens for implantation in the eye, which comprises a generally planar, oblong lens body having two opposed longer sides and two opposed shorted sides, each shorter side having a stabilizer formation disposed laterally therealong and extending peripherally outwardly therefrom, and a separate, generally planar, continuous and uninterrupted ring shaped collapsible filament, tension frame having an outer boundary edge and an inner edge defining an oblong aperture with two opposed longer sides and two opposed shorter sides and sized and shaped for overlapping registry with the lens body, the frame including two opposed longer side oblong planar wing members defining light masking means and two opposed shorter side collapsibly deformable pairs of closely side by side locally flexible but essentially unstretchable linear tension filaments laterally interconnecting correspondingly adjacent ends of the wing members to form the frame and define the aperture therewithin.

each opposed pair of filaments being sized and arranged to receive and grippingly embrace therebetween a corresponding stabilizer formation for mounting the lens body under positive tension thereby on the frame with the lens body longer sides in overlapping relation to the adjacent portions of the wing members along the aperture longer sides for assembling the two pieces as a self connected, generally stiff planar unit.

* * * * *